US012709593B2

(12) United States Patent
Arai et al.

(10) Patent No.: US 12,709,593 B2
(45) Date of Patent: Aug. 18, 2026

(54) PURIFICATION DEVICE

(71) Applicant: NIPPON SHOKUBAI CO., LTD., Osaka (JP)

(72) Inventors: Shogo Arai, Himeji (JP); Masashi Mukae, Himeji (JP); Hiroki Wada, Himeji (JP); Toshiya Fukumoto, Himeji (JP); Takayuki Matsuda, Himeji (JP); Toyofumi Sakai, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 629 days.

(21) Appl. No.: 18/253,684

(22) PCT Filed: Nov. 17, 2021

(86) PCT No.: PCT/JP2021/042245
§ 371 (c)(1),
(2) Date: May 19, 2023

(87) PCT Pub. No.: WO2022/107812
PCT Pub. Date: May 27, 2022

(65) Prior Publication Data
US 2024/0010600 A1 Jan. 11, 2024

(30) Foreign Application Priority Data
Nov. 20, 2020 (JP) ................................ 2020-193566

(51) Int. Cl.
*B01D 9/02* (2006.01)
*B01D 9/00* (2006.01)
(Continued)

(52) U.S. Cl.
CPC ............ *C07C 51/43* (2013.01); *B01D 9/0004* (2013.01); *B01D 9/02* (2013.01); *B01D 21/262* (2013.01)

(58) Field of Classification Search
CPC ........ C07V 51/43; B01D 9/0004; B01D 9/02; B01D 21/262; C07C 51/43
See application file for complete search history.

(56) References Cited

U.S. PATENT DOCUMENTS 4,508,553 A 4/1985 Thijssen et al.
4,557,741 A 12/1985 Van Pelt
(Continued)

FOREIGN PATENT DOCUMENTS

CN 201625434 U 11/2010
CN 102471214 A 5/2012
(Continued)

*Primary Examiner* — Robert M Kunemund
(74) *Attorney, Agent, or Firm* — Dickinson Wright PLLC

(57) ABSTRACT

The present invention aims to provide a compound purification apparatus capable of providing a high purity compound in high yield and at low cost. The present invention relates to an apparatus for purifying a compound, the purification apparatus including: a crystallizing unit including a crystal forming section; and a wash column including a mechanism that forcibly transfers crystals, the crystallizing unit including N tanks connected in series, wherein N is 2 or greater, a 1st tank is a most downstream tank, a (N)th tank is a most upstream tank, at least the 1st tank is a crystallization tank including a cooling mechanism, and a 2nd and subsequent tanks are each a crystallization tank or a ripening tank, the purification apparatus including a line that feeds a compound-containing liquid to be purified to at least one of the N tanks, the wash column including: a line that sends a product out; and a line that returns a mother liquor to the crystallizing unit, with the line that returns a mother liquor to the crystallizing unit being connected to at least the (N)th (Continued)

tank, the crystallizing unit including: a line that feeds a slurry from the (N)th tank to the wash column; a line that sends a slurry from a tank among the 1st to (N−1)th tanks to the next upstream tank; and a line that is provided to each of the 1st to (N−1)th tanks and that sends thereto a mother liquor withdrawn from an upstream tank, wherein at least one of the lines that send a slurry from a tank among the 1st to (N−1)th tanks to the next upstream tank is a line that sends a slurry from a tank to the next upstream tank via a solid-liquid separator and that has a line that returns a mother liquor from which crystals are removed in the solid-liquid separator to the tank where the slurry came from, and wherein the line that is provided to each of the 1st to (N−1)th tanks and that sends thereto a mother liquor withdrawn from an upstream tank is a line that directly sends a mother liquor withdrawn from a tank one upstream or a line that sends a mother liquor withdrawn from a tank one upstream via a solid-liquid separator, the purification apparatus further including a line that sends a mother liquor to the outside of the purification apparatus.

12 Claims, 3 Drawing Sheets

(51) Int. Cl.
*B01D 21/26* (2006.01)
*C07C 51/43* (2006.01)

(56) References Cited

U.S. PATENT DOCUMENTS 4,588,414 A 5/1986 Takegami et al.
4,666,456 A 5/1987 Thijssen et al.
4,787,985 A * 11/1988 Roodenrijs .......... B01D 9/0036 210/260
6,362,347 B1 * 3/2002 Baumann .................. C25B 3/25 549/307
7,319,166 B2 1/2008 Hammon et al.
7,557,245 B2 * 7/2009 Nordhoff ................ C07C 51/43 562/600
9,597,609 B2 * 3/2017 Jansen ................ B01D 9/0059
2002/0065447 A1 5/2002 Yoshida et al.
2002/0159935 A1 10/2002 Jansen
2003/0060661 A1 3/2003 Eck et al.
2003/0175159 A1 9/2003 Heilek et al.
2006/0013748 A1 1/2006 Nordhoff et al.
2011/0105791 A1 5/2011 Kuppinger et al.
2012/0108857 A1 5/2012 Sakamoto et al.
2012/0232233 A1 9/2012 Kuppinger et al.
2013/0053522 A1 2/2013 Kuppinger et al.
2013/0253149 A1 9/2013 Kuppinger et al.

FOREIGN PATENT DOCUMENTS

CN 104024221 A 9/2014
CN 207085389 U 3/2018
EP 1469926 B1 1/2019
GB 2023564 A 1/1980
GB 2262052 A 6/1993
JP S58-128105 A 7/1983
JP S59-66305 A 4/1984
JP S64-70103 A 3/1989
JP H06-91103 A 4/1994
JP 2002-114718 A 4/2002
JP 2002-370002 A 12/2002
JP 2003-530376 A 10/2003
JP 2004-203713 A 7/2004
JP 2005-232134 A 9/2005
JP 2010-501526 A 1/2010
JP 2013-184948 A 9/2013
TW 201438814 A 10/2014
TW I590866 B 7/2017
WO WO2012/093937 A1 7/2012
WO WO2014/108285 A1 7/2014

* cited by examiner

PURIFICATION DEVICE

TECHNICAL FIELD

The present invention relates to purification apparatuses that can be suitable for purification of industrially produced compounds.

BACKGROUND ART

Currently, various compounds are industrially widely produced and used. Industrially produced compounds are required to be high-quality products with reduced impurities depending on their uses. Various studies have been made on better purification techniques for obtaining such high-quality products.

Disclosed compound purification techniques include a purification method in which cooling crystallization tanks each having a clarification section in the upper part and a vertical purification column having a clarification section in the upper part and a heater in the lower part are connected in series; crystals are formed in each crystallization tank and sent to a side of a crystallization tank that is connected to the purification column; the crystals sent from the crystallization tank are gravity-settled in the purification column, while a portion of the crystals heated and melted by the heater at the lower part of the purification column is raised as a reflux liquid and is brought into contact with the crystals during gravity-settling, and whereby the crystals are washed (see Patent Literatures 1 and 2). Another disclosed technique is a method for purifying acrylic acid in which a suspension containing acrylic acid crystals produced in a crystallization tank and a crude acrylic acid melt is sent to a wash column, the crystals are forcibly transferred in the wash column and melted in the lower part of the column to obtain a melt, and the melt is used as a washing liquid to wash the crystals in the wash column (see Patent Literature 3). Still another disclosed technique is a purification method in which the purity of acrylic acid is increased by repeating multiple times suspension crystallization or layer crystallization of an aqueous solution containing acrylic acid (see Patent Literature 4).

CITATION LIST

Patent Literature

Patent Literature 1: JP S59-66305 A
Patent Literature 2: JP H06-91103 A
Patent Literature 3: JP 2003-530376 T
Patent Literature 4: JP 2010-501526 T

SUMMARY OF INVENTION

Technical Problem

Although various purification techniques have been disclosed as described above, in industrial production, high-yield and low-cost production of high purity compounds has been required. As a result of studies, the present inventors found that the purification apparatuses using a gravity settling wash column described in Patent Literatures 1 and 2 cannot achieve an industrially sufficient purification effect and an industrially sufficient production volume in the purification of an organic compound that forms crystals with a relatively small particle size or a low purity crude compound solution. Also, the purification apparatus described in Patent Literature 3 fails to achieve a high yield in crystallization, leading to an increase in the operating cost of treating a crystallization residue. In order to achieve a high yield in crystallization, the purity of a crude compound solution to be subjected to the crystallization is required to be high, disadvantageously leading to an increase in the purification cost of pre-crystallization. In the method described in Patent Literature 4 in which crystallization is repeated multiple times, the purity of the crude compound solution to be subjected to crystallization may be low. However, the method includes a step of once melting the crystals and a step of discharging a mother liquor during crystallization, which disadvantageously leads to complication of equipment and thus increases equipment investment cost and energy consumption. The present invention has been made in view of the above-mentioned current state of art and aims to provide a compound purification apparatus capable of providing a high purity compound in high yield and at low cost.

Solution to Problem

The present inventors studied purification apparatuses capable of providing a high purity compound in high yield and at low cost, and found that a purification apparatus having the following configuration can provide a high purity compound in high yield and at low cost. In a purification apparatus having a configuration in which N tanks including at least one crystallization tank and optionally a ripening tank, which are connected in series, and the most upstream tank (a crystallization tank or a ripening tank) is connected to the wash column, at least one of lines that send a slurry from a crystallization tank or a ripening tank to the next upstream tank is a line that sends a slurry via a solid-liquid separator; the purification apparatus further includes a line that returns a mother liquor from which crystals have been removed in the solid-liquid separator to the tank where the slurry came from and a line that returns a mother liquor from the washing column to at least the (N)th tank in the crystallizing unit; each of the 1st to (N−1)th tanks in the crystallizing unit includes at least one of a line that directly sends a mother liquor withdrawn from a tank one upstream or a line that sends a mother liquor withdrawn from a tank one upstream via a solid-liquid separator; and the purification apparatus further includes a line that sends a mother liquor to the outside of the purification apparatus.

That is, the present invention relates to an apparatus for purifying a compound, the purification apparatus including:

a crystallizing unit including a crystal forming section; and a wash column including a mechanism that forcibly transfers crystals, the crystallizing unit including N tanks connected in series, wherein N is 2 or greater, a 1st tank is a most downstream tank, a (N)th tank is a most upstream tank, at least the 1st tank is a crystallization tank including a cooling mechanism, and a 2nd and subsequent tanks are each a crystallization tank or a ripening tank, the purification apparatus including a line that feeds a compound-containing liquid to be purified to at least one of the N tanks, the wash column including:

a line that sends a product out; and a line that returns a mother liquor to the crystallizing unit, with the line that returns a mother liquor to the crystallizing unit being connected to at least the (N)th tank, the crystallizing unit including:

a line that feeds a slurry from the (N)th tank to the wash column;

a line that sends a slurry from a tank among the 1st to (N−1)th tanks to the next upstream tank; and a line that is provided to each of the 1st to (N−1)th tanks and that sends thereto a mother liquor withdrawn from an upstream tank, wherein at least one of the lines that send a slurry from a tank among the 1st to (N−1)th tanks to the next upstream tank is a line that sends a slurry from a tank to the next upstream tank via a solid-liquid separator and that has a line that returns a mother liquor from which crystals are removed in the solid-liquid separator to the tank where the slurry came from, and wherein the line that is provided to each of the 1st to (N−1)th tanks and that sends thereto a mother liquor withdrawn from an upstream tank is a line that directly sends a mother liquor withdrawn from a tank one upstream or a line that sends a mother liquor withdrawn from a tank one upstream via a solid-liquid separator, the purification apparatus further including a line that sends a mother liquor to the outside of the purification apparatus.

Preferably, each of the 1st to (N−1)th tanks in the crystallizing unit includes a line that sends a slurry from a tank to the next upstream tank via a solid-liquid separator and a line that returns at least a portion of a mother liquor discharged from the solid-liquid separator to the tank where the slurry came from.

Preferably, at least one of the lines that are provided to the 1st to (N−1)th tanks and that send thereto a mother liquor withdrawn from an upstream tank is a line that sends a mother liquor withdrawn from a tank one upstream via a solid-liquid separator.

Preferably, at least one of solid-liquid separators each provided in a line that sends a slurry from a downstream tank to an upstream tank includes a line that returns a mother liquor to the tank where the slurry came from, and at least one additional line that sends a mother liquor, wherein the at least one additional line is connected to a tank that is downstream from the tank where the slurry came from and/or to the outside of the purification apparatus.

Preferably, at least one of the 1st to (N−1)th tanks in the crystallizing unit includes a line that directly sends a mother liquor withdrawn from a tank one upstream.

Preferably, the purification apparatus further includes a line that sends a mother liquor from the 1st tank in the crystallizing unit to the outside of the purification apparatus via a solid-liquid separator.

Preferably, the cooling mechanism is of a type that contents of the tank are cooled outside the tank.

The wash column may or may not include a mechanical mechanism that scrapes off a crystal bed.

Preferably, the compound is (meth)acrylic acid.

Preferably, in the crystallizing unit, at least a line that sends a slurry from the (n−1)th tank to the (N)th tank among lines that send a slurry from a tank to the next upstream tank is a line that sends a slurry from a tank to the next upstream tank via a solid-liquid separator, and wherein the solid-liquid separator in the line that sends a slurry from the (n−1)th tank to the (N)th tank is a basket centrifuge or a decanter centrifuge.

Advantageous Effects of Invention

The apparatus for purifying a compound of the present invention can provide high-purity compounds in high yield with the amount of discharged crystallization residue being reduced, even in purification of an organic compound that forms crystals with a relatively small particle size or purification of a low purity crude compound solution. Further, since the amount of washing liquid in the wash column can be reduced, the operating cost of the apparatus can be reduced.

DESCRIPTION OF EMBODIMENTS

Figure 1:
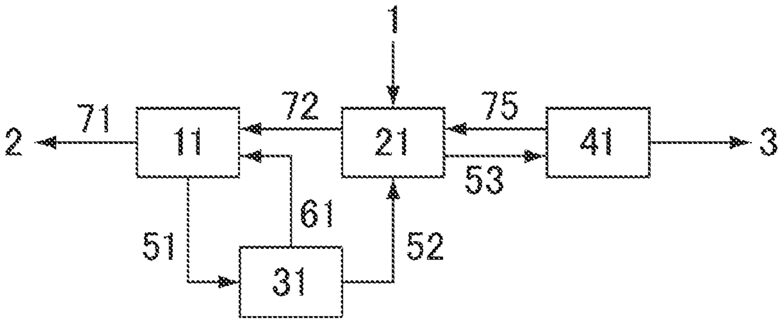
FIG. 1 is a diagram illustrating an example of a purification apparatus of the present invention.

The present invention is described in detail below.

A combination of two or more of individual preferred embodiments of the present invention described below is also a preferred embodiment of the present invention.

The purification apparatus of the present invention includes a crystallizing unit that includes N (N≥2) tanks connected in series and a wash column that forcibly transfers crystals. In the crystallizing unit, at least the 1st tank is a crystallization tank including a cooling mechanism, and the 2nd and subsequent tanks are each a crystallization tank or a ripening tank. The (N)th tank is connected to the wash column. A slurry is sent in order from any one of the downstream tanks to the next upstream tank, and is sent from the (N)th tank to the wash column. Further, at least one of the lines that send a slurry in order from any one of the downstream tanks to the next upstream tank is a line that sends a slurry from a tank to the next upstream tank via a solid-liquid separator and the solid-liquid separator has a line that returns at least a portion of the mother liquor discharged from the solid-liquid separator to the tank where the slurry came from. Furthermore, in the purification apparatus of the present invention, each of the 1st to (N−1)th tanks in the crystallizing unit has at least one of a line that directly sends a mother liquor withdrawn from a tank one upstream or a line that sends a mother liquor withdrawn from a tank one upstream via a solid-liquid separator, and the purification apparatus further includes a line that sends a mother liquor to the outside of the purification apparatus.

In the tanks including at least one crystallization tank and optionally a ripening tank, which are connected in series, a slurry suspension containing crystals of the compound and a mother liquor is sent in order from any of the tanks to the next upstream tank, and the mother liquor is sent from an upstream tank to a downstream tank with being brought into countercurrent contact with crystals. Thereby, the purity of the crystals and the purity of the mother liquor can be higher upstream. Here, the purity of the crystals and the purity of the mother liquor can be improved more effectively by using as many solid-liquid separators as possible for concentrating and sending a slurry to upstream tanks.

Thus, in the purification apparatus of the present invention, the line that sends a mother liquor to the outside of the purification apparatus is preferably a line that sends a mother liquor from the most downstream tank to the outside of the purification apparatus. Thereby, a smaller amount of a low purity mother liquor (crystallization residue) in which impurities are concentrated can be discharged from the most downstream tank, and thus, a high purity compound can be obtained in high yield.

In the wash column, a portion of the liquid obtained by heating and melting the purified crystals is brought into countercurrent contact with the crystal bed as a washing liquid to provide high purity crystals. The amount of the washing liquid can be reduced by feeding high purity crystals and a high purity mother liquor from the (N)th tank to the wash column. As a result, the amount of crystals produced in the crystallization tank can be reduced, and the operating cost of a refrigerator can be reduced.

In the case where a plurality of tanks are used and the crystals in the slurry are sent upstream while the crystals are condensed to increase the purity of the crystals and the purity of the mother liquor, in order to bring the mother liquor into countercurrent contact with the crystals and to adjust the liquid level of each tank, a line that sends a mother liquor not containing crystals from upstream to downstream or a line that sends a mother liquor not containing crystals from a tank in the purification apparatus, preferably from the most downstream tank, to the outside of the purification apparatus.

A known method in this respect is a conventional technique in which an area for crystal settling is provided in the upper part of a tank, and the mother liquor containing no crystals (hereinafter sometimes referred to as a clear mother liquor) is overflowed and sent from the tank to a downstream tank, and directly discharged from the most downstream tank to the outside of the purification apparatus. This technique advantageously does not require a liquid sending pump, leading to facilitation of adjustment of the liquid level in each tank, while the technique disadvantageously requires an area for crystal setting in the upper part of a tank, leading to complication of the structure of the tank.

In particular, in the case of purifying a compound that forms fine crystals or a low purity compound solution, each of which has a low settling speed of crystals, an excessively large tank is required to design an area for crystal settling. When the crystals are too fine to form an area for crystal settling well, the crystals are sent downstream, which may reduce the purification effect of the apparatus.

Further, the purification apparatus of the present invention includes line(s) that send a slurry in order from any of the downstream tanks to the next upstream tank, and at least one of the line(s) has a line that sends a slurry from a tank to the next upstream tank via a solid-liquid separator. Such a structure can prevent crystals from being sent to the downstream tanks, efficiently increase the purity in the upstream tanks, and facilitate the purification in the next step (wash column).

The percentage of the lines that send a slurry from a downstream tank to the next upstream tank via a solid-liquid separator is preferably 60% or more of (N−1) lines that send a slurry from a downstream tank to the next upstream tank. Most preferably, the percentage is 100%. In other words, all of the (N≥1) lines that send a slurry from a downstream tank to the next upstream tank are lines that send a slurry from a downstream tank to the next upstream tank via a solid-liquid separator.

At least the line that sends a slurry from the (N−1)th tank to the (N)th tank among the lines that send a slurry from a downstream tank to the next upstream tank is preferably a line that sends a slurry via a solid-liquid separator.

In the crystallizing unit, a tank that includes a line that sends a slurry from a tank to the next upstream tank via a solid-liquid separator has a line that returns at least a portion of the mother liquor discharged from the solid-liquid separator to the tank where the slurry came from. The concentrated slurry containing crystals separated in the solid-liquid separator is sent from a tank to the next upstream tank, and at least a portion of the remaining mother liquor is returned to the tank where the slurry came from.

Further, the crystallizing unit includes, as the line that is provided to each of the 1st to (N−1)th tanks and that sends thereto a mother liquor withdrawn from an upstream tank, at least one of a line that directly sends a mother liquor withdrawn from a tank one upstream or a line that sends a mother liquor withdrawn from a tank one upstream via a solid-liquid separator. The presence of such line(s) can keep the liquid level in the tank one upstream constant.

In the purification apparatus of the present invention, at least one of the 1st to (N−1)th tanks in the crystallizing unit preferably has a line that directly sends a mother liquor withdrawn from a tank one upstream. More preferably, the (N−1)th tank has a line that directly sends a mother liquor withdrawn from a tank one upstream ((N)th tank). The reason why the presence of a line that directly sends a mother liquor from the (N)th tank to the (N−1)th tank is preferred will be described later.

When the crystallizing unit includes a tank that includes a line that sends a mother liquor withdrawn from a tank one upstream via a solid-liquid separator, the crystals are effectively prevented from being sent downstream from an upper stream tank to the next downstream tank owing to solid-liquid separation. Even when the purification apparatus is used to purify a compound having a low settling speed of crystals, the purification efficiency of the purification apparatus can be kept high. Thus, preferably, at least one of the lines that are provided to the 1st to (N−1)th tanks and that send thereto a mother liquor withdrawn from an upstream tank is a line that sends a mother liquor withdrawn from a tank one upstream via a solid-liquid separator.

Preferably, when the crystallizing unit includes a line that sends a mother liquor withdrawn from a tank one upstream via a solid-liquid separator, the solid-liquid separator in the line that sends a slurry from a tank to the next upstream tank is shared for use, from the viewpoint of the cost of the purification apparatus itself and the operating cost of the apparatus. This can reduce the number of devices such as solid-liquid separators or liquid sending pumps.

In such a case, the apparatus may have the configuration in which a solid-liquid separator provided in a line A that sends a slurry from a tank to the next upstream tank includes a line B that returns a mother liquor from the solid-liquid separator to the tank where the slurry came from, and the line B has at least one additional line that sends a mother liquor, with the at least one additional line being connected to a tank that is one downstream from the tank where the slurry came from. In addition, a line may be branched from the at least one additional line and may be connected to a tank that is two or more downstream from the tank where the slurry came from, in addition to the tank that is one downstream from the tank where the slurry came from. The at least one additional line may also be connected to the outside of the purification apparatus.

In a preferred embodiment of the purification apparatus of the present invention, the crystallizing unit has such a configuration, that is, a configuration in which at least one of solid-liquid separators each provided in a line that sends a slurry from a tank to an upstream tank includes a line that returns a mother liquor to the tank where the slurry came from and at least one additional line that sends a mother liquor, with the at least one additional line being connected to a tank that is downstream from the tank where the slurry came from and/or to the outside of the purification apparatus.

The percentage of the solid-liquid separators having such an additional line is preferably 30% or more, more preferably 60% or more, still more preferably 100%, of the solid-liquid separators each provided in a line that sends a slurry from a downstream tank to an upstream tank.

The solid-liquid separator may be a commonly used means such as a basket centrifuge, a decanter centrifuge, a liquid cyclone, or a filter. An example of a basket centrifuge is an Escher-Wyss push type centrifuge available from Tsukishima Kikai Co., Ltd. Examples of a decanter centrifuge include a bird decanter centrifuge available from Tsukishima Kikai Co., Ltd. and a screw decanter centrifuge available from IHI Corporation.

In the case of using a basket centrifuge, the concentration of crystals in the cake after solid-liquid separation is preferably 80% or higher, more preferably 85% or higher, still more preferably 90% or higher. In the case of using a decanter centrifuge, the concentration of crystals after concentration is preferably 40% or higher, more preferably 50% or higher, still more preferably 60% or higher.

In the case of using a liquid cyclone, the concentration of crystals in the slurry after concentration is preferably 25% or higher, more preferably 30% or higher, still more preferably 35% or higher. When the slurry concentration is increased too much, the fluidity decreases to increase the risk of pipe clogging. Thus, the slurry concentration after concentration is preferably 55% or lower, more preferably 50% or lower, still more preferably 45% or lower.

In the case of using a basket centrifuge or a decanter centrifuge as a solid-liquid separator, high initial investment is required and operating costs are high, while owing to the high slurry (crystal) concentration efficiency, the purification efficiency of the compound is advantageously increased. In the case of using a liquid cyclone, due to the low slurry (crystal) concentration efficiency, a large number of tanks are required in the crystallizing unit in order to achieve a sufficient purification effect, while advantageously, initial investment is low, operating costs are reduced, and troubles originating from the rotating machine are avoided.

As described above, in the crystallizing unit, preferably, at least a line that sends a slurry from the (n−1)th tank to the (N)th tank among lines that send a slurry from a tank to the next upstream tank is a line that sends a slurry from a tank to the next upstream tank via a solid-liquid separator. In that case, preferably, the solid-liquid separator in the line that sends a slurry from the (n−1)th tank to the (N)th tank is a basket centrifuge or a decanter centrifuge.

The crystallizing unit includes tanks including at least one crystallization tank and optionally a ripening tank. The total number of the crystallization tanks and the ripening tanks is not limited. In order to sufficiently increase the purity of crystals and the purity of a mother liquor, in the case of using a basket centrifuge or a decanter centrifuge as a solid-liquid separator, the total number is preferably 2 or more, and in other cases, the total number is preferably 3 or more. The larger the number of tanks is, the higher the effect of increasing the purity of crystals and the purity of a mother liquor is, while too large a number of tanks disadvantageously leads to an increase in equipment investment cost and an increase in power consumption of equipment attached to the tanks, such as pumps or stirrers. Therefore, the total number of the crystallization tanks and the ripening tanks is preferably 6 or less regardless of the type of solid-liquid separator. The total number is more preferably 5 or less.

In the crystallizing unit, as long as at least one of the tanks is a crystallization tank, the other tanks may each be a crystallization tank or a ripening tank. The number of ripening tanks in the crystallizing unit is preferably 0 to 2, more preferably 0 to 1.

Each tank in the crystallizing unit preferably has a structure capable of forming a clear mother liquor layer in the upper part of the tank. When any of the 1st to (N−1)th tanks in the crystallizing unit has a line that directly sends a mother liquor withdrawn from a tank one upstream, the line preferably directly sends the overflowed clear mother liquor layer in the upper part of the tank. Also, in a preferred embodiment of the purification apparatus of the present invention, the line that sends a mother liquor to the outside of the purification apparatus is a line that sends the overflowed mother liquor to the outside of the purification apparatus.

As described above, the purification apparatus of the present invention preferably includes a line that sends a mother liquor to the outside of the purification apparatus from the most downstream tank (1st tank) in the crystallizing unit. In a preferred embodiment of the purification apparatus of the present invention, this line is a line that sends the overflowed clear mother liquor layer in the upper part of the 1st tank in the crystallizing unit to the outside of the purification apparatus.

When each tank in the crystallizing unit does not form a clear mother liquor layer in the upper part, a solid-liquid separator is provided. Thereby, the slurry withdrawn from the tank is separated into a mother liquor and crystals in the solid-liquid separator, and the mother liquor is sent from the tank to the next downstream tank or a two or more-downstream tank. The mother liquor separated in the solid-liquid separator may be discharged to the outside of the purification apparatus. In a preferred embodiment of the purification apparatus of the present invention, the purification apparatus includes a line that sends a mother liquor from the 1st tank in the crystallizing unit to the outside of the purification apparatus via a solid-liquid separator.

Preferably, 30% or more, more preferably, 60% or more of the 1st to (N−1)th tanks in the crystallizing unit, most preferably, all of the 1st to (N−1)th tanks in the crystallizing unit have a structure in which the mother liquor is sent from a tank to the next downstream tank (and/or to a two or more-downstream tank) via a solid-liquid separator and/or a structure in which the mother liquor is discharged to the outside of the crystallizing unit. This can reduce the size of each tank to reduce the investment amount and construction area. As described above, preferably, the solid-liquid separator in a line that sends a slurry from a tank to the next upstream tank is shared for use as the solid-liquid separator in this case, from the cost point of view.

The (N)th tank preferably has a larger capacity than any of the downstream tanks in order to hold/age the slurry to be sent to the wash column, and in the (N)th tank, the purity of the slurry is higher and crystals are likely to grow to a larger crystal size compared to in any of the downstream tanks. Thus, an area for crystal settling, i.e., a clear mother liquor layer, in the upper part of the tank is relatively easily designed. The (N)th tank preferably has a structure in which the mother liquor is overflowed and directly sent to the downstream tanks.

Each crystallization tank in the crystallizing unit in the present invention may be any tank that includes a cooling mechanism and cools the compound solution for precipitation of crystals so that a slurry containing crystals and a mother liquor is produced. The cooling mechanism is roughly classified into a system where a cooling jacket directly attached to the tank directly cools the inside of the tank to form crystals and a system where a cooling mechanism and the tank separated from each other are connected with a pipe and crystals are formed through cooling under circulation.

The system where a cooling jacket is directly attached to the tank has the advantage of reducing the number of devices, but requires a large tank for a larger heat transfer area. When a higher productivity is required, the size of the tank is excessively large, which is disadvantageous in terms of initial investment and installation area.

In this respect, in the case where the size of the tank is limited or in the case of purification of compounds which requires high productivity, a crystallization tank is preferably of a type that the contents of the tank are cooled outside the tank. In such a case where the tank is connected to a cooling mechanism with a pipe, a portion of the compound solution (or crystal-containing slurry) in the tank is sent to the cooling mechanism to form crystals in the cooling mechanism, and a slurry containing the formed crystals is returned to the tank, the heat transfer area can be easily increased by increasing the number of cooling mechanisms, and the crystallization tank can be easily scaled up.

The cooling mechanism in this case is not limited as long as it can cool the compound solution to precipitate crystals. Preferred examples of the cooling mechanism include those that can have a large heat transfer area, such as a shell-and-tube heat exchanger and a spiral heat exchanger, and those that form crystals by scraping cooled surfaces, such as a cooling disk crystallizer and a scraping cooling crystallizer.

The cooling disk crystallizer cools the compound solution to precipitate crystals and scrapes off the precipitated crystals. The cooling disk crystallizer may be, for example, one including a cylinder and cooling plates that separate the inside of the cylinder and having a configuration in which crystals are formed on the wall surfaces of the cooling plates and a stirring blade with a wiper is rotated in the cylinder to scrape off the crystals.

The scraping cooling crystallizer cools the compound solution to precipitate crystals and scrapes off the precipitated crystals. The scraping cooling crystallizer may be, for example, one including a double pipe and having a configuration in which a cooling medium is passed through the outer pipe and the compound solution (or slurry containing crystals) in the tank is passed through the inner pipe to form crystals on the wall surface of the inner pipe, and a shaft having a scraping blade is rotated in the inner pipe to scrape off the crystals.

The crystallizing unit in the present invention may or may not include a ripening tank, and preferably includes a ripening tank. The ripening tank in the present invention does not have a cooling mechanism that precipitates crystals. The crystals of the compound are grown by holding in the ripening tank for a certain period of time. The crystals grown as uniform as possible are sent to the wash column. Thereby, impurities can be efficiently removed in the wash column and a high purity compound can be obtained in high yield. Thus, the ripening tank is preferably a tank that sends liquid to the wash column, that is, the (N)th tank.

The ripening tank is not limited as long as it can hold the crystals of the compound suspended in the tank. When the crystals are held for a certain period of time, fine crystals are melted by Ostwald ripening and large crystals grow even larger, so that the crystal size distribution becomes narrower. Thereby, the purification efficiency in the wash column can be further improved. Even in a crystallization tank, the same effect as in the ripening tank can be expected by holding crystals for a certain period of time.

A slurry containing crystals of the compound is sent from the (N)th tank in the crystallizing unit to the wash column in the purification apparatus of the present invention, and the crystals are washed to give high-purity-compound crystals as a product. In the wash column in a preferred embodiment of the present invention, when having a higher specific gravity than the mother liquor, crystals move downwards in the column to form a crystal bed. A portion of crystals is withdrawn from the crystal bed while being suspended in a circulation liquid (a washing liquid circulating in the wash column) liquid, and heated and melted to obtain a melt. A portion of the circulation liquid containing the melt is withdrawn as a product. A portion of the rest of the circulation liquid (washing liquid) is brought into countercurrent contact with the crystal bed to wash the crystals. The mother liquor in the wash column is returned to the crystallizing unit through a line that returns a mother liquor to the crystallizing unit.

The line that returns a mother liquor to the crystallizing unit is connected to at least the (N)th tank, and may also be connected from the (N)th tank to any of the downstream tanks. The purification apparatus may further include a line that returns a portion of the mother liquor to the wash column again.

When having a lower specific gravity than the mother liquor, crystals move upwards in the column contrary to the above-described case, and in the upper part of the column, the crystal bed is suspended, melt, and a product is withdrawn.

The wash column in the purification apparatus of the present invention forcibly transfers the crystal bed. Specific examples thereof include a mechanical wash column in which crystals are compacted with a piston to form a crystal bed and the crystal bed is transferred, and a hydraulic wash column in which a slurry is sent to a column with a pump, a mother liquor is withdrawn through a filter in the column to form a crystal bed, and the crystal bed is transferred. The operating principles of these wash columns are described in the book Melt Crystallization (edited by Joachim Ulrich, Heike Glade, Shaker Verlag, Aachen 2003).

The wash column is not limited as long as it can wash crystals, and may be either a mechanical wash column or a hydraulic wash column. Mechanical wash columns operate with high stability and purify a compound with high efficiency. Hydraulic wash columns achieve a high production capacity per column cross-sectional area and include a small number of driving parts to cause few problems arising from equipment. When an easily polymerizable substance is purified, use of a hydraulic wash column having a small number of driving parts may prevent or reduce the generation of polymers in the wash column.

An example of a preferred embodiment of the wash column is one having a mechanical mechanism that scrapes off a crystal bed (see U.S. Pat. No. 3,872,009 A). A wash column having a mechanism that forcibly transfers a crystal bed employs a system in which the purified crystal bed is scraped off with a scraper or the like, resuspended, and then melted.

Another example of a preferred embodiment of the wash column is one having no mechanical mechanism that scrapes off a crystal bed (see U.S. Pat. No. 7,425,273 B2). In this system, the crystal bed is scraped off by the dynamic pressure of the circulation liquid. In this system, since a sliding surface such as a shaft seal is absent, the generation of polymers due to liquid accumulation, heat from sliding, and the like may be prevented or reduced when an easily polymerizable substance is purified.

The compound solution, which is the liquid to be purified to be fed to the purification apparatus of the present invention, may be fed to any of the tanks in the crystallizing unit, preferably to any of the 2nd and subsequent tanks. The most suitable tank to which the solution is fed depends on the composition of the liquid to be fed, the crystallization yield, and the concentration efficiency of crystals in a solid-liquid separator, and may be appropriately determined according to these.

The crystallization temperature in each crystallization tank in the purification apparatus of the present invention may be appropriately adjusted according to the type of compound to be purified. The crystallization temperature is generally −1° C. to −15° C., preferably −1.5° C. to −13.5° C., more preferably −3.5° C. to −12.5° C., still more preferably −5° C. to −11.5° C. from the melting point of the pure compound. When the compound to be purified is (meth)acrylic acid, the crystallization temperature is preferably 0° C. to 12° C., more preferably 1° C. to 10° C., still more preferably 2° C. to 8.5° C.

When the temperature in the crystallization tank is high, high purity crystals are produced, while when the crystallization tank includes a scraping cooling crystallizer, which is described later, the crystallization tank may require a large amount of power for scraping off crystals in the crystallization tank or may have other disadvantages. Also, too large a temperature difference between the cooling medium and the inside of the crystallization tank may cause a problem of blocking of the scraper or other problems when the crystallization tank includes a scraping cooling crystallizer, for example, which may lead to a difficulty in continuous operation.

In response to such a problem, when the temperature in the crystallization tank is high, the temperature difference between the cooling medium and the inside of the crystallization tank is required to be reduced, thereby reducing the amount of crystals produced per heat transfer area. When the temperature in the crystallization tank is low, low purity crystals are produced, while when the crystallization tank includes a scraping cooling crystallizer, the crystallization tank requires only a small amount of power for scraping crystals, and the scraper is less likely to be blocked even when the temperature difference between the cooling medium and the inside of the crystallization tank is large. As a result, the temperature difference between the cooling medium and the inside of the crystallization tank may be increased to increase the amount of crystals produced per heat transfer area. However, when the crystallization temperature is too low, crystals with smaller particle sizes, which are less likely to settle, are produced.

The residence time of the compound in the crystallization tank or the ripening tank may be adjusted to an appropriate time according to the type of the compound to be purified. From the viewpoint of the yield of the compound obtained after purification, the efficiency of purification, and equipment investment cost, the residence time is roughly from 0.02 to 6 hours.

The residence time in the (N)th tank is preferably longer than a certain duration in order to reduce the particle size distribution of the slurry to be sent to the wash column and to reduce the reflux ratio (washing liquid flow rate/purified acrylic acid flow rate) in the wash column. The residence time is preferably 0.5 to 6 hours, more preferably 1 to 5 hours, still more preferably 1.2 to 4.5 hours.

The 1st to (N−1)th tanks do not necessarily require a long residence time because they are not connected to the wash column. A shorter residence time allows the size of the tank itself to be reduced, which is advantageous in terms of equipment investment cost. Therefore, the residence time in each of the 1st to (N−1)th tanks is preferably 0.03 to 4 hours, more preferably 0.04 to 3 hours, still more preferably 0.05 to 2 hours, most preferably 0.1 to 1.5 hours.

The residence time of the compound in each crystallization tank herein refers to the residence time in the cooling mechanism inside or outside the tank when the crystallization tank is of a type that the contents of the tank are cooled outside the tank, which will be described later. The residence time in each tank is calculated by dividing the combined capacity of the tank and an external cooling mechanism by the combined amount of the slurry fed from the tank to an upstream tank or the wash column and the liquid sent from the tank to a downstream tank or discharged from the tank to the outside of the purification apparatus.

The purification apparatus of the present invention may be used to purify any compound. The purification apparatus is suitable for purification of (meth)acrylic acid because the method can also be suitable for purification of crystals with poor settling properties as described above. Thus, in a preferred embodiment of the present invention, the compound to be purified with the purification apparatus of the present invention is (meth)acrylic acid.

In this case, the compound solution to be fed to the purification apparatus of the present invention is a (meth) acrylic acid aqueous solution or a crude (meth)acrylic acid solution. The (meth)acrylic acid aqueous solution refers to a solution in which (meth)acrylic acid is dissolved in water. The crude (meth)acrylic acid solution refers to a solution composed of (meth)acrylic acid and containing impurities such as by-products produced during the production of the (meth)acrylic acid. These can be obtained, for example, as follows: propylene and isobutylene are subjected to a vapor phase oxidation reaction to obtain a compound gas as a reaction product, and the compound gas is collected in an absorption column and optionally distilled. They are not limited to those synthesized in-house and may be procured from outside sources. The aqueous (meth)acrylic acid solution or the crude (meth)acrylic acid solution is cooled, for example, to obtain a slurry containing (meth)acrylic acid crystals.

Examples of the by-products include acids such as propionic acid, acetic acid, maleic acid, benzoic acid, and acrylic acid dimers; aldehydes such as acrolein, furfural, formaldehyde, and glyoxal; acetone; and protoanemonin. In addition, solvents such as toluene and methyl butyl ketone may be contained.

Herein, the term "(meth)acrylic acid" refers to acrylic acid and/or methacrylic acid.

Examples of the purification apparatus of the present invention are shown in FIGS. 1 to 8.

FIG. 1 illustrates an apparatus including a crystallizing unit that includes one crystallization tank and one ripening tank. The apparatus includes a line that directly sends a mother liquor from the ripening tank to the next downstream crystallization tank, and a line that directly discharges a residue (mother liquor) from the crystallization tank, which is the most downstream tank.

A compound solution 1 to be fed to the purification apparatus is introduced into a ripening tank 21. The slurry containing the crystals precipitated through cooling in the crystallization tank 11 that includes a cooling mechanism is sent to a solid-liquid separator 31 through a line 51. In the solid-liquid separator 31, the slurry is separated into a mother liquor and a concentrated crystal slurry. The concentrated crystal slurry is sent to the adjacent ripening tank 21 through a line 52, and the mother liquor is returned to the crystallization tank 11 through a line 61. A residue 2 is discharged from the crystallization tank 11 through a line 71 to the outside of the purification apparatus. Thereby, the liquid level in the crystallization tank 11 is adjusted. The crystals are grown in the ripening tank 21, and the crystal slurry is sent to a mechanical wash column 41 through a line 53. In order to adjust the liquid level in the ripening tank 21, the mother liquor is directly sent from the ripening tank 21 to the crystallization tank 11 through a line 72.

In the mechanical wash column 41, the crystals are compacted with a piston to form a crystal bed. The crystal bed is scraped off in the lower part of the column, suspended in a circulation liquid, and heated and melted. A portion of the circulation liquid containing the melt is sent out as a high purity compound 3. A portion of the rest of the circulation liquid (washing liquid) is returned to the mechanical wash column 41 and brought into countercurrent contact with the crystal bed to wash the crystals. Also, the mother liquor in the wash column is returned to the ripening tank 21 through a line 75 that returns a mother liquor to the crystallizing unit. The compound is purified in this manner to obtain a high purity compound.

Figure 2:
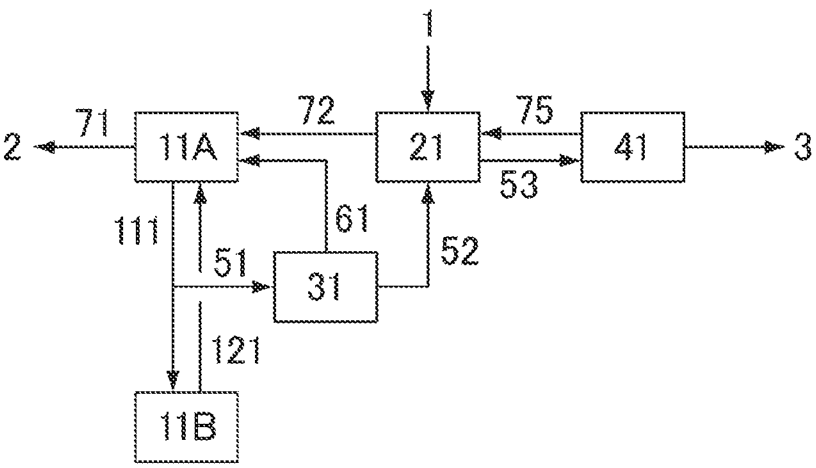
FIG. 2 is a diagram illustrating another example of the purification apparatus of the present invention.

FIG. 2 illustrates an apparatus including a crystallizing unit that includes one crystallization tank and one ripening tank. The apparatus includes a line that directly sends a mother liquor from the ripening tank to the next downstream crystallization tank, and a line that directly discharges a residue (mother liquor) from the crystallization tank, which is the most downstream tank. The crystallization tank is of a type that the contents of the tank are cooled outside the tank. The following describes only parts different from the purification apparatus of FIG. 1.

The crystallization tank 11 includes a tank 11A and a cooling mechanism 11B provided outside the tank, which are connected by lines 111 and 121. The compound solution (or the slurry containing crystals of the compound) sent from the tank 11A to the cooling mechanism 11B through the line 111 is cooled using the cooling mechanism 11B to precipitate crystals, and the slurry containing the crystals is sent to the tank 11A through the line 121. A portion of the slurry containing the crystals of the compound is sent from the tank 11A to the cooling mechanism 11B through the line 111, and the rest of the slurry is sent to the solid-liquid separator 31 through the line 51.

Figure 3:
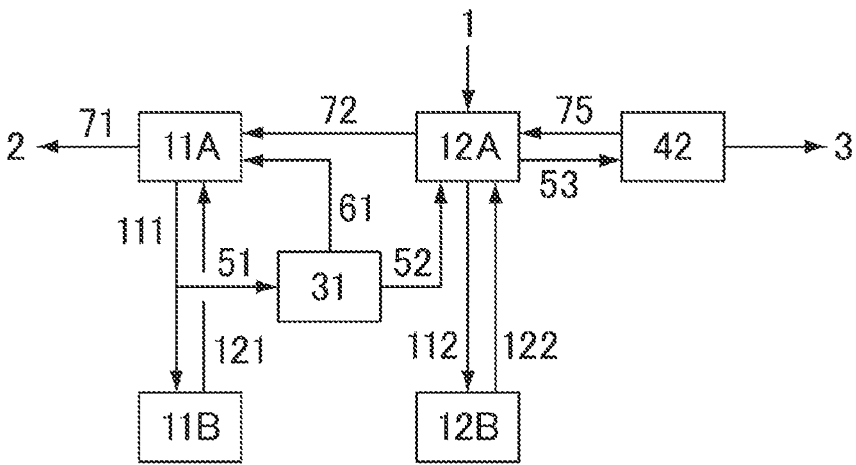
FIG. 3 is a diagram illustrating another example of the purification apparatus of the present invention.

FIG. 3 illustrates an apparatus including a crystallizing unit that includes two crystallization tanks. The apparatus includes a line that directly sends a mother liquor from a crystallization tank 12 to the next downstream crystallization tank 11, and a line that directly discharges a residue (mother liquor) from the crystallization tank 11, which is the most downstream tank. The wash column is a hydraulic wash column and includes a mechanical mechanism that scrapes off the crystal bed. The following describes only parts different from the purification apparatus of FIG. 1.

The compound solution 1 to be fed to the purification apparatus is introduced into the crystallization tank 12.

The crystallization tank 11 includes the tank 11A and the cooling mechanism 11B provided outside the tank, which are connected by the lines 111 and 121. The compound solution (or the slurry containing crystals of the compound) sent from the tank 11A to the cooling mechanism 11B through the line 111 is cooled using the cooling mechanism 11B to precipitate crystals, and the slurry containing the crystals is sent to the tank 11A through the line 121. A portion of the slurry containing the crystals of the compound is sent from the tank 11A to the cooling mechanism 11B through the line 111, and the rest of the slurry is sent to the solid-liquid separator 31 through the line 51.

The crystallization tank 12 also includes a tank 12A and a cooling mechanism 12B provided outside the tank, which are connected by lines 112 and 122. A portion of the slurry containing the crystals of the compound is sent from the tank 12A to the cooling mechanism 12B through the line 112, and sent back to the tank 12A through the line 122.

The crystal slurry is sent from the crystallization tank 12 to a hydraulic wash column 42 through the line 53. The crystal bed is scraped off in the lower part of the hydraulic wash column 42 with a mechanical mechanism (scraper), withdrawn while being suspended in a circulation liquid, and heated and melted to obtain a melt. A portion of the circulation liquid containing the melt is sent out as the high purity compound 3. A portion of the rest of the circulation liquid (washing liquid) is returned to the hydraulic wash column 42 and brought into countercurrent contact with the crystal bed to wash the crystals.

Figure 4:
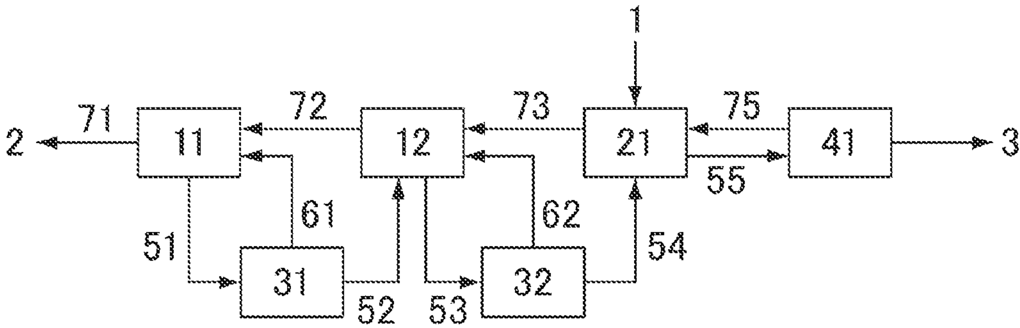
FIG. 4 is a diagram illustrating another example of the purification apparatus of the present invention.

FIG. 4 illustrates an apparatus including a crystallizing unit that includes two crystallization tanks and one ripening tank. The apparatus includes a line that directly sends a mother liquor withdrawn from a tank one upstream in every position between any two adjacent tanks of the three tanks and a line that directly discharges a residue (mother liquor) from the most downstream tank. The following describes only parts different from the purification apparatus of FIG. 1.

The slurry containing the crystals precipitated through cooling in the crystallization tank 11 that includes a cooling mechanism is sent to the solid-liquid separator 31 through the line 51. In the solid-liquid separator 31, the slurry is separated into a mother liquor and a concentrated crystal slurry. The concentrated crystal slurry is sent to the adjacent crystallization tank 12 through the line 52, and the mother liquor is returned to the crystallization tank 11 through the line 61. The residue 2 is discharged from the crystallization tank 11 through the line 71 to the outside of the purification apparatus. Thereby, the liquid level in the crystallization tank 11 is adjusted. The same operation as in the crystallization tank 11 is performed in the crystallization tank 12, and the crystal-containing slurry is sent from the crystallization tank 12 to a solid-liquid separator 32 through the line 53. In the solid-liquid separator 32, the slurry is separated into a mother liquor and a concentrated crystal slurry. The concentrated crystal slurry is sent to the adjacent ripening tank 21 through a line 54, and the mother liquor is returned to the crystallization tank 12 through a line 62. In order to adjust the liquid level in the crystallization tank 12, the mother liquor is directly sent from the crystallization tank 12 to the crystallization tank 11 through the line 72. The crystals are grown in the ripening tank 21, and the crystal slurry is sent to the mechanical wash column 41 through a line 55. In order to adjust the liquid level in the ripening tank 21, the mother liquor is directly sent from the ripening tank 21 to the crystallization tank 12 through a line 73 that connects the ripening tank 21 and the crystallization tank 12.

Figure 5:
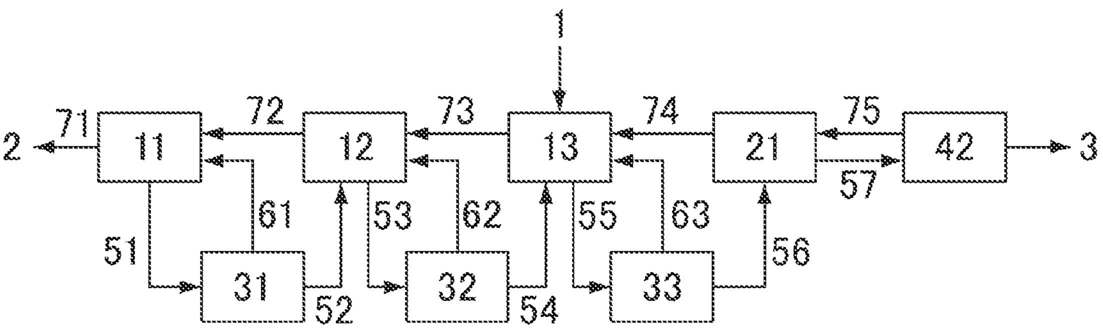
FIG. 5 is a diagram illustrating another example of the purification apparatus of the present invention.

FIG. 5 illustrates an apparatus including a crystallizing unit that includes three crystallization tanks and one ripening tank. The apparatus includes a line that directly sends a mother liquor withdrawn from a tank one upstream in every position between any two adjacent tanks of the four tanks and a line that directly discharges a residue (mother liquor) from the most downstream tank. The wash column is a hydraulic wash column and includes a mechanical mechanism that scrapes off the crystal bed. The following describes only parts different from the purification apparatus of FIG. 4.

The compound solution 1 to be fed to the purification apparatus is introduced into a crystallization tank 13. A crystal-containing slurry is sent to the solid-liquid separator 32 through the line 53 from the crystallization tank 12, which is a one-upstream tank from the most downstream tank. In the solid-liquid separator 32, the slurry is separated into a mother liquor and a concentrated crystal slurry. The concentrated crystal slurry is sent to the adjacent crystallization tank 13 through the line 54, and the mother liquor is returned to the crystallization tank 12 through the line 62. In order to adjust the liquid level in the crystallization tank 12, the mother liquor is directly sent from the crystallization tank 12 to the crystallization tank 11 through the line 72. The same operation as in the crystallization tank 12 is performed in the crystallization tank 13, and the crystal-containing slurry is sent from the crystallization tank 13 to a solid-liquid separator 33 through the line 55. In the solid-liquid separator 33, the slurry is separated into a mother liquor and a concentrated crystal slurry. The concentrated crystal slurry is sent to the adjacent ripening tank 21 through a line 56, and the mother liquor is returned to the crystallization tank 13 through a line 63. In order to adjust the liquid level in the crystallization tank 13, the mother liquor is directly sent from the crystallization tank 13 to the crystallization tank 12 through the line 73. The crystals are grown in the ripening tank 21, and then, the crystal slurry is sent to the hydraulic wash column 42 through a line 57. In order to adjust the liquid level in the ripening tank 21, the mother liquor is directly sent from the ripening tank 21 to the crystallization tank 13 through a line 74 that connects the ripening tank 21 and the crystallization tank 13.

The crystal bed is scraped off in the lower part of the hydraulic wash column 42 with a mechanical mechanism (scraper), withdrawn while being suspended in a circulation liquid, and heated and melted to obtain a melt. A portion of the circulation liquid containing the melt is sent out as the high purity compound 3. A portion of the rest of the circulation liquid (washing liquid) is returned to the hydraulic wash column 42 and brought into countercurrent contact with the crystal bed to wash the crystals.

Figure 6:
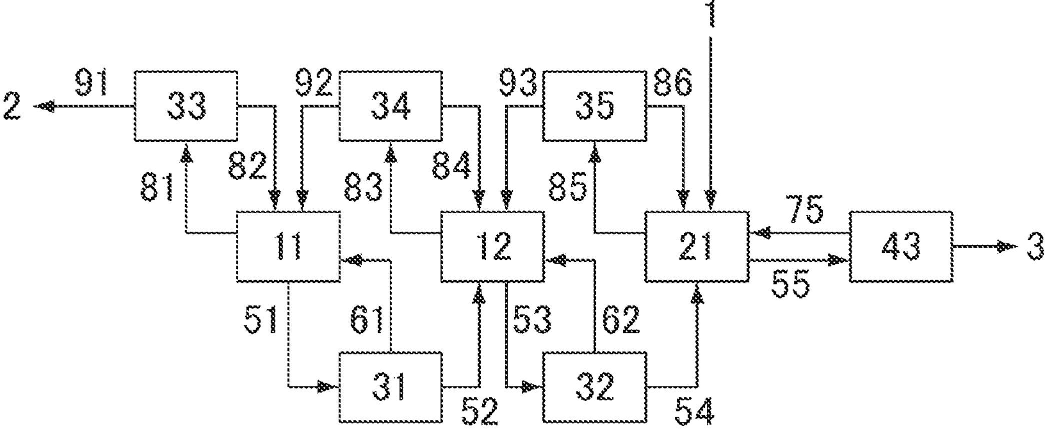
FIG. 6 is a diagram illustrating another example of the purification apparatus of the present invention.

FIG. 6 illustrates an apparatus including a crystallizing unit that includes two crystallization tanks and one ripening tank. The apparatus includes a line that sends a mother liquor withdrawn from a tank one upstream via a solid-liquid separator in every position between any two adjacent tanks of the three tanks, and a line that discharges a residue from the most downstream tank via a solid-liquid separator. The following describes only parts different from the purification apparatus of FIG. 4.

The crystallization tank 11 of FIG. 6 includes the solid-liquid separator 33 that separates a residue from the slurry in the crystallization tank instead of the line that directly discharges a residue. The slurry withdrawn from the crystallization tank 11 is sent to the solid-liquid separator 33 through a line 81, the residue 2 separated in the solid-liquid separator 33 is discharged to the outside of the purification apparatus, and the remaining crystals are returned to the crystallization tank 11, and thereby the liquid level in the crystallization tank 11 is adjusted.

The crystallization tank 12 includes a solid-liquid separator 34 instead of the line that directly sends a mother liquor to the crystallization tank 11. The slurry withdrawn from the crystallization tank 12 is sent to the solid-liquid separator 34 through a line 83, the mother liquor separated in the solid-liquid separator 34 is sent to the crystallization tank 11 to adjust the liquid level, and the remaining crystals are returned to the crystallization tank 12.

The ripening tank 21 includes a solid-liquid separator 35 instead of the line that directly sends a mother liquor to the crystallization tank 12. The slurry withdrawn from the ripening tank 21 is sent to the solid-liquid separator 35 through a line 85, the mother liquor separated in the solid-liquid separator 35 is sent to the crystallization tank 12 to adjust the liquid level, and the remaining crystals are returned to the ripening tank 21.

The wash column 43 is a hydraulic wash column and includes no mechanical mechanism that scrapes off the crystal bed.

Figure 7:
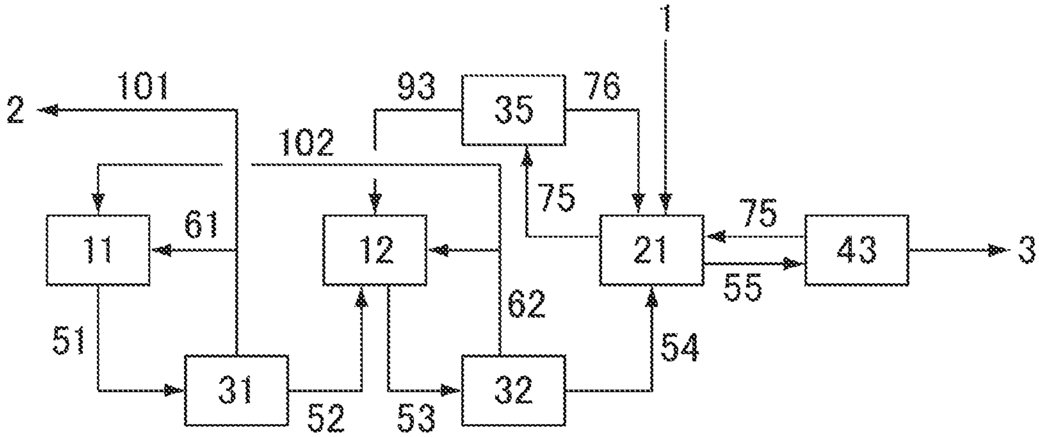
FIG. 7 is a diagram illustrating another example of the purification apparatus of the present invention.

FIG. 7 illustrates an apparatus including a crystallizing unit that includes two crystallization tanks and one ripening tank. The apparatus includes a line that sends a mother liquor withdrawn from a tank one upstream via a solid-liquid separator in every position between any two adjacent tanks of the three tanks, and a line that discharges a residue from the most downstream tank via a solid-liquid separator. The solid-liquid separator that separates a mother liquor from the slurry withdrawn from the 2nd crystallization tank and sends the mother liquor to the most downstream (1st) crystallization tank and the solid-liquid separator that separates a residue to be discharged from the most downstream (1st) crystallization tank to the outside of the purification apparatus are each shared for use as the corresponding solid-liquid separators each in a line that sends a slurry from a tank to the next upstream tank. The following describes only parts different from the purification apparatus of FIG. 6.

In the apparatus of FIG. 7, the slurry containing the crystals precipitated in the crystallization tank 11 through cooling is sent to the solid-liquid separator 31 through the line 51. In the solid-liquid separator 31, the slurry is separated into a mother liquor and a concentrated crystal slurry. The concentrated crystal slurry is sent to the adjacent crystallization tank 12 through the line 52. A portion of the mother liquor separated in the solid-liquid separator 31 is returned to the crystallization tank 11 through the line 61, and the rest of the mother liquor is discharged to the outside of the purification apparatus through an additional line 101 connected to the line 61.

The slurry containing the crystals precipitated in the crystallization tank 12 through cooling is sent to the solid-liquid separator 32 through the line 53. In the solid-liquid separator 32, the slurry is separated into a mother liquor and a concentrated crystal slurry. The concentrated crystal slurry is sent to the adjacent ripening tank 21 through the line 54. A portion of the mother liquor separated in the solid-liquid separator 32 is returned to the crystallization tank 12 through the line 62, and the rest of the mother liquor is sent to the crystallization tank 11 through an additional line 102 connected to the line 62.

The flow from the line 51 to the solid-liquid separator 31 to the lines 61 and 101 in the purification apparatus of FIG. 7 corresponds to the flow from the line 81 to the solid-liquid separator 33 to lines 82 and 91 in the apparatus of FIG. 6. The solid-liquid separator 31 in the line that sends a slurry to an upstream tank is shared for use as the solid-liquid separator 33. Thereby, the number of devices is reduced. Similarly, the flow from the line 53 to the solid-liquid separator 32 to the lines 62 and 102 corresponds to the flow from the line 83 to the solid-liquid separator 34 to lines 84 and 92 in the apparatus of FIG. 6. The solid-liquid separator 32 in the line that sends a slurry to an upstream tank is shared for use as the solid-liquid separator 34. Thereby, the number of devices is reduced.

Figure 8:
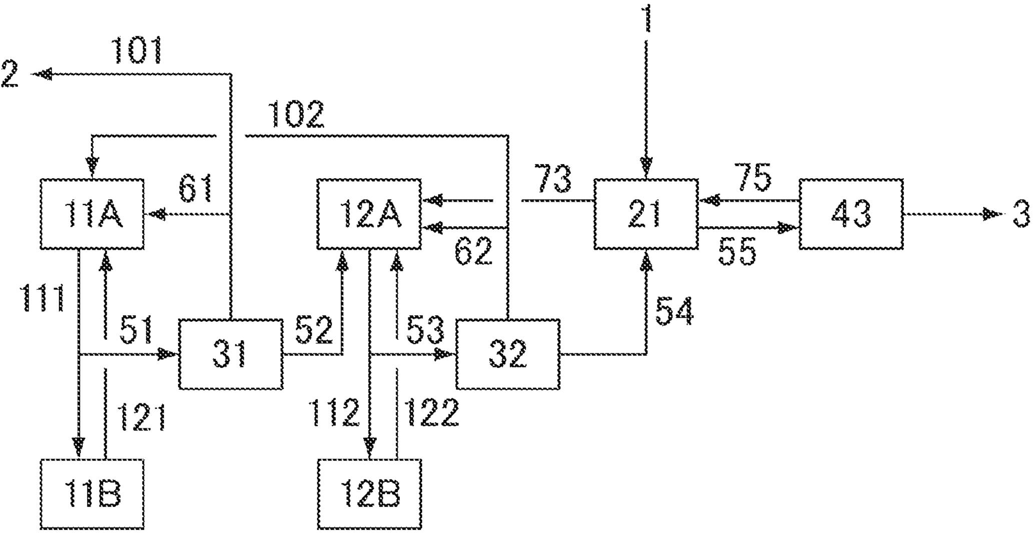
FIG. 8 is a diagram illustrating another example of the purification apparatus of the present invention.

FIG. 8 illustrates an apparatus including a crystallizing unit that includes two crystallization tanks and one ripening tank. The apparatus includes a line that sends a mother liquor from the 2nd crystallization tank to the most downstream (1st) crystallization tank via a solid-liquid separator, a line that discharges a residue from the most downstream tank via a solid-liquid separator, and a line that directly sends a mother liquor from the ripening tank to the 2nd crystallization tank. The solid-liquid separator that separates a mother liquor from the slurry withdrawn from the 2nd crystallization tank and sends the mother liquor to the most downstream crystallization tank and the solid-liquid separator that separates a residue to be discharged from the most downstream crystallization tank to the outside of the purification apparatus are each shared for use as the corresponding solid-liquid separators each in a line that sends a slurry from a tank to the next upstream tank. The crystallization tank is of a type that the contents of the tank are cooled outside the tank. The following describes only parts different from the purification apparatus of FIG. 7.

In the apparatus of FIG. 8, the crystallization tank 11 includes the tank 11A and the cooling mechanism 11B provided outside the tank, which are connected by the lines 111 and 121. The compound solution (or the slurry containing crystals of the compound) sent from the tank 11A to the cooling mechanism 11B through the line 111 is cooled using the cooling mechanism 11B to precipitate crystals, and the slurry containing the crystals is sent to the tank 11A through the line 121. A portion of the slurry containing the crystals of the compound is sent from the tank 11A to the cooling mechanism 11B through the line 111, and the rest of the slurry is sent to the solid-liquid separator 31 through the line 51.

The crystallization tank 12 also includes the tank 12A and the cooling mechanism 12B provided outside the tank, which are connected by the lines 112 and 122. A portion of the slurry containing the crystals of the compound is sent from the tank 12A to the cooling mechanism 12B through the line 112, and the rest of the slurry is sent to the solid-liquid separator 32 through the line 53.

The apparatus of FIG. 8 includes the line 73 that directly sends a mother liquor from the ripening tank 21 to the tank 12A instead of the line that sends a mother liquor from the ripening tank 21 to the crystallization tank 12 via the solid-liquid separator 35 in the apparatus of FIG. 7.

REFERENCE SIGNS LIST

- 1: compound solution
- 2: residue
- 3: high purity compound
- 11 to 13: crystallization tank including cooling mechanism
- 11A, 12A: tank
- 11B, 12B: cooling mechanism
- 21: ripening tank
- 31 to 35: solid-liquid separator
- 41: mechanical wash column
- 42: hydraulic wash column (including mechanical mechanism that scrapes off crystal bed)
- 43: hydraulic wash column (including no mechanical mechanism that scrapes off crystal bed)
- 51 to 57: line that sends slurry (or crystals) from downstream tank to upstream tank or wash column
- 61 to 63: line that returns mother liquor separated from slurry in solid-liquid separator to tank where the slurry came from
- 71: line that directly discharges residue (mother liquor) from most downstream tank to the outside of purification apparatus
- 72 to 74: line that directly sends mother liquor from upstream tank to next downstream tank
- 75: line that returns mother liquor from wash column to crystallizing unit
- 81 to 86: line that returns crystals separated in solid-liquid separator from slurry withdrawn from tank to tank where the slurry came from
- 91: line that discharges residue (mother liquor) separated in solid-liquid separator from slurry withdrawn from tank to the outside of purification apparatus
- 92, 93: line that sends mother liquor separated in solid-liquid separator from slurry withdrawn from tank to next downstream tank
- 101: additional line that discharges, to the outside of purification apparatus, portion of mother liquor separated in solid-liquid separator from slurry withdrawn from most downstream tank
- 102: additional line that sends, to most downstream tank, portion of mother liquor separated in solid-liquid separator from slurry withdrawn from 2nd tank
- 111, 121, 112, 122: line that connects tank and cooling mechanism in crystallization tank which is of a type that contents of tank are cooled outside tank

The invention claimed is:

1. An apparatus for purifying a compound, the purification apparatus comprising:

a crystallizing unit including a crystal forming section; and a wash column including a mechanism that forcibly transfers crystals, the crystallizing unit including N tanks connected in series, wherein N is 2 or greater, a 1st tank is a most downstream tank, a (N)th tank is a most upstream tank, at least the 1st tank is a crystallization tank including a cooling mechanism, and a 2nd and subsequent tanks are each a crystallization tank or a ripening tank, the purification apparatus including a line that feeds a compound-containing liquid to be purified to at least one of the N tanks, the wash column including:

a line that sends a product out; and a line that returns a mother liquor to the crystallizing unit, with the line that returns a mother liquor to the crystallizing unit being connected to at least the (N)th tank, the crystallizing unit including:

a line that feeds a slurry from the (N)th tank to the wash column;

a line that sends a slurry from a tank among the 1st to (N-1)th tanks to the next upstream tank; and a line that is provided to each of the 1st to (N-1)th tanks and that sends thereto a mother liquor withdrawn from an upstream tank, and a line that returns a mother liquor from the wash column to the (N)th tank of the crystallizing unit without passing through any other crystallization tank or ripening tank, wherein at least one of the lines that send a slurry from a tank among the 1st to (N-1)th tanks to the next upstream tank is a line that sends a slurry from a tank to the next upstream tank via a solid-liquid separator and that has a line that returns a mother liquor from which crystals are removed in the solid-liquid separator to the tank where the slurry came from, and wherein the line that is provided to each of the 1st to (N-1)th tanks and that sends thereto a mother liquor withdrawn from an upstream tank is a line that directly sends a mother liquor withdrawn from a tank one upstream or a line that sends a mother liquor withdrawn from a tank one upstream via a solid-liquid separator, the purification apparatus further including a line that sends a mother liquor to the outside of the purification apparatus.

2. The purification apparatus according to claim 1, wherein each of the 1st to (N-1)th tanks in the crystallizing unit includes a line that sends a slurry from a tank to the next upstream tank via a solid-liquid separator and a line that returns at least a portion of a mother liquor discharged from the solid-liquid separator to the tank where the slurry came from.

3. The purification apparatus according to claim 1, wherein at least one of the lines that are provided to the 1st to (N-1)th tanks and that send thereto a mother liquor withdrawn from an upstream tank is a line that sends a mother liquor withdrawn from a tank one upstream via a solid-liquid separator.

4. The purification apparatus according to claim 1, wherein at least one of solid-liquid separators each provided in a line that sends a slurry from a downstream tank to an upstream tank includes a line that returns a mother liquor to the tank where the slurry came from, and at least one additional line that sends a mother liquor, wherein the at least one additional line is connected to a tank that is downstream from the tank where the slurry came from and/or to the outside of the purification apparatus.

5. The purification apparatus according to claim 1, wherein at least one of the 1st to (N-1)th tanks in the crystallizing unit includes a line that directly sends a mother liquor withdrawn from a tank one upstream.

6. The purification apparatus according to claim 1, further comprising a line that sends a mother liquor from the 1st tank in the crystallizing unit to the outside of the purification apparatus via a solid-liquid separator.

7. The purification apparatus according to claim 1, wherein the cooling mechanism is of a type that contents of the tank are cooled outside the tank.

8. The purification apparatus according to claim 1, wherein the wash column includes a mechanical mechanism that scrapes off a crystal bed.

9. The purification apparatus according to claim 1, wherein the wash column does not include a mechanical mechanism that scrapes off a crystal bed.

10. The purification apparatus according to claim 1, wherein the compound is (meth)acrylic acid.

11. The purification apparatus according to claim 1, wherein in the crystallizing unit, at least a line that sends a slurry from the (n-1)th tank to the (N)th tank among lines that send a slurry from a tank to the next upstream tank is a line that sends a slurry from a tank to the next upstream tank via a solid-liquid separator, and wherein the solid-liquid separator in the line that sends a slurry from the (n-1)th tank to the (N)th tank is a basket centrifuge or a decanter centrifuge.

12. The purification apparatus according to claim 1, wherein the (N)th tank included in the crystallization apparatus has a larger capacity than any of the downstream tanks, and further wherein the (N)th tank has a structure in which the mother liquor is overflowed and directly sent to the downstream tanks.

* * * * *